United States Patent [19]  
Curran

[11] Patent Number: 4,959,495  
[45] Date of Patent: Sep. 25, 1990

[54] PROCESS FOR THE PREPARATION OF INTERMEDIATES USED TO PRODUCE AMINOTHIAZOLOXIMINO CEPHALOSPORINS

[75] Inventor: William V. Curran, Pearl River, N.Y.

[73] Assignee: American Cyanamid Company, Stamford, Conn.

[21] Appl. No.: 375,108

[22] Filed: Jun. 30, 1989

Related U.S. Application Data

[62] Division of Ser. No. 163,599, Mar. 3, 1988, abandoned, which is a division of Ser. No. 890,000, Jul. 29, 1986, abandoned.

[51] Int. Cl.$^5$ .............................................. C07C 131/00  
[52] U.S. Cl. ..................................... 562/560; 560/168; 540/227  
[58] Field of Search ........................................ 562/560

[56] References Cited

U.S. PATENT DOCUMENTS

| 4,029,781 | 6/1977 | Berger | 560/168 |
| 4,152,432 | 5/1979 | Heymes | 560/168 |
| 4,205,180 | 5/1980 | Ochiai | 560/168 |
| 4,298,259 | 11/1981 | Ueda | 562/567 |
| 4,371,531 | 2/1983 | Takaya | 514/207 |
| 4,480,120 | 10/1984 | Jewell | 560/168 |
| 4,845,257 | 7/1989 | Naito | 560/168 |

FOREIGN PATENT DOCUMENTS

61-10569 1/1986 Japan .  
61-50973 3/1986 Japan .

OTHER PUBLICATIONS

Imanishi, J. Labelled Compd. Radiopharm., 23, pp. 951–956, (1986).

Primary Examiner—Michael L. Shippen  
Attorney, Agent, or Firm—T. S. Szatkowski

[57] ABSTRACT

A process is disclosed for the preparation of intermediates useful in the synthesis of aminothiazoloximino cephalosporins.

1 Claim, No Drawings

PROCESS FOR THE PREPARATION OF INTERMEDIATES USED TO PRODUCE AMINOTHIAZOLOXIMINO CEPHALOSPORINS

This is a divisional of application Ser. No. 163,599, filed Mar. 3, 1988, which in turn is a divisional of application Ser. No. 890,000, filed July 28, 1986, now abandoned.

This invention relates to the intermediates, and the synthesis thereof, which are useful in the preparation of an important class of antibiotics; namely, the aminothiazoloximino cephalosporins represented by the following general structure:

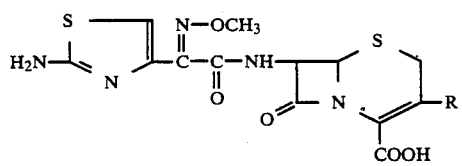

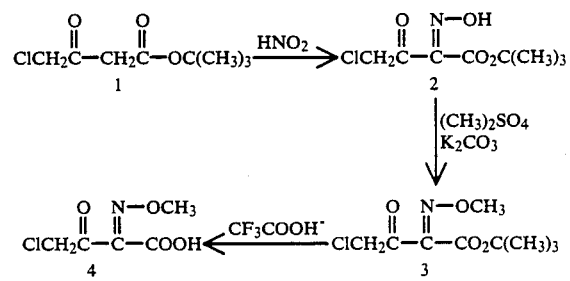

Nitrosation of the t-butyl ester 1 gave the oximino derivative 2 as an oil which was methylated with dimethyl sulfate and potassium carbonate in acetone to afford the methoxime 3. Compound 3 was purified by chromatography to give the pure (Z)-methoximo compound as an oil which crystallized on standing.

Treatment of compound 3 with trifluoroacetic acid produced the desired (Z)-methoximo acid 4 as a white crystalline compound. Compounds 2, 3 and 4 are new compounds.

Scheme II

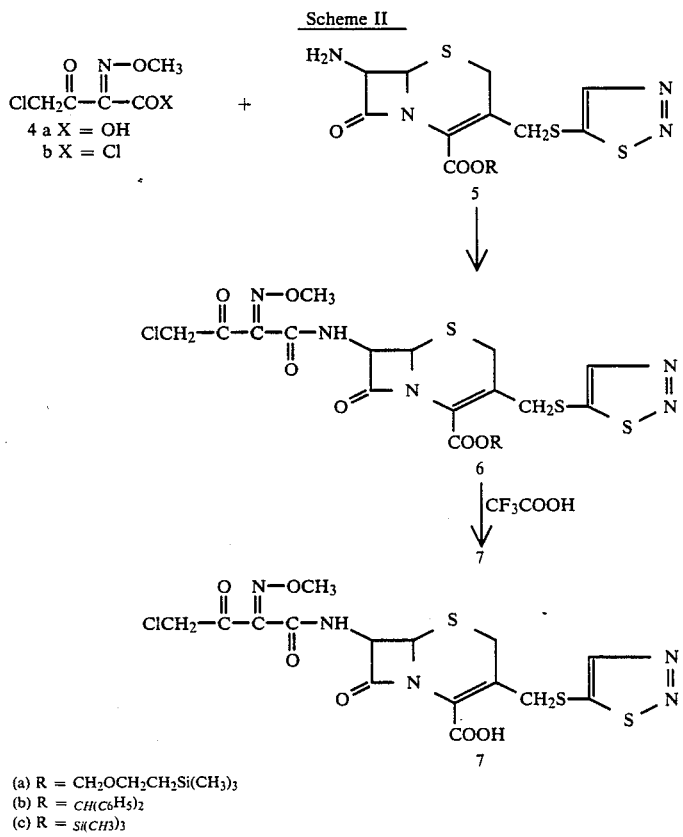

(a) R = CH$_2$OCH$_2$CH$_2$Si(CH$_3$)$_3$
(b) R = CH(C$_6$H$_5$)$_2$
(c) R = Si(CH$_3$)$_3$

The intermediates of the present invention are also useful for the synthesis of such cephalosporin compounds containing a radioactive moiety in the aminothiazole portion of the molecule. Such radio-labelled compounds are important for pharmacological evaluation.

According to the present invention, hovel intermediates are generated pursuant to reactions summarized in Scheme I.

The condensation of the chlorooximino acid 4 with the 7-aminocephalosporin compound, for example compound 5, can be carried out in several different ways. Using a protected derivative of compound 5 for example the trimethylsilylethoxymethylester 5a or the benzhydryl ester 5b the reaction can be carried out using 1-ethoxycarbonyl-2-ethoxy-1,3-dihydroquinoline to afford the protected derivatives 6a and 6b. Removal of the protecting groups by trifluoroacetic acid affords the desired intermediate 7. Alternatively, compound 4 can be converted to the acid chloride 4b and condensed with the trimethylsilylester 5c, which is procuced in situ. The usual work-up and purification of this reaction gives compound 7.

J. Antibiotics, 34, 186 (1981) which is illustrated in Scheme IV. Compound 10 (prepared in situ by reaction of diketene with chlorine) was condensed with the 7-

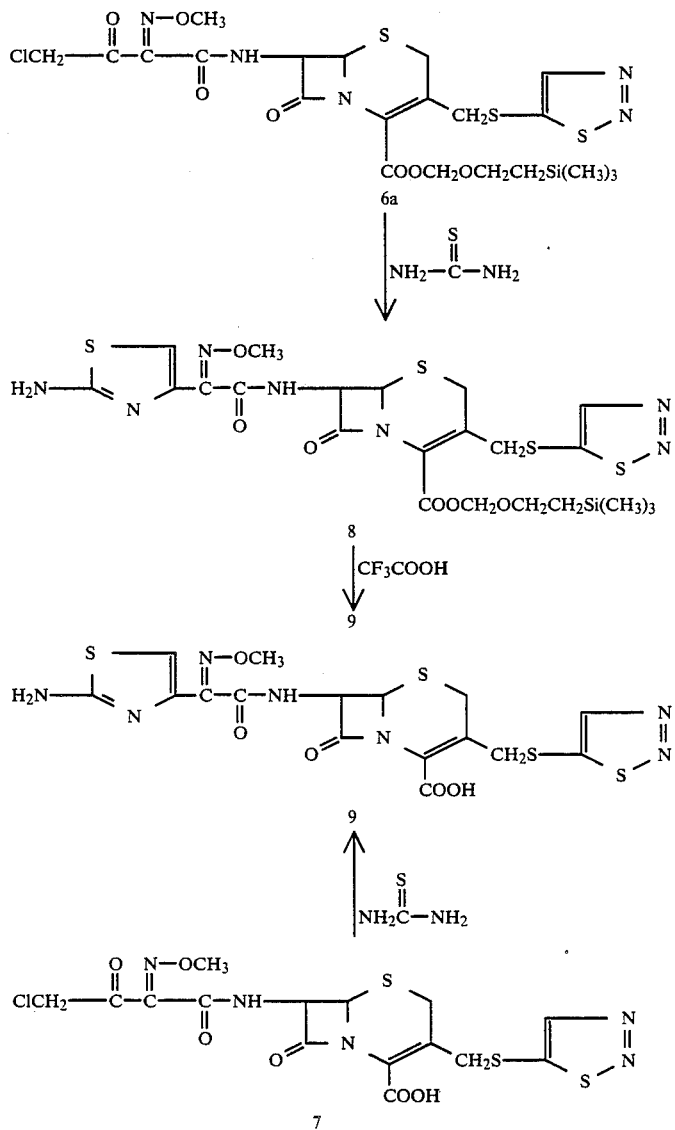

The reaction of the protected compound 6a with thiourea gives the trimethylsilylethoxymethyl ester of the cephalosporin 8 which can readily be converted to the desired final product, compound 9 by treatment with trifluoroacetic acid. Similarly compound 9 can be prepared directly by the condensation of compound 7 with thiourea.

Alternatively these reactions can be carried out using radioactive thiourea resulting in a radio-labelled cephalosporin antibiotic.

Preparation of the intermediate compound 7 was first attempted using the method described by Ochiai, et al.

aminocephalosporanic acid 5 to afford compound 10 which converted to the oxime 11 with nitrous acid. Attempted methylation of compound 11 by the usual procedures gave a mixture of products from which little or none of the desired compound 7 could be isolated. In all probability the complicating factor in this last reaction is the presence of the 1,2,3-thiadiazole moiety in the 3' position of the cephalosporin. Under the reaction conditions this heterocyclic group probably also reacts with the alkylating agent dimethyl sulfate thus accounting for the poor yield of the desired product 7.

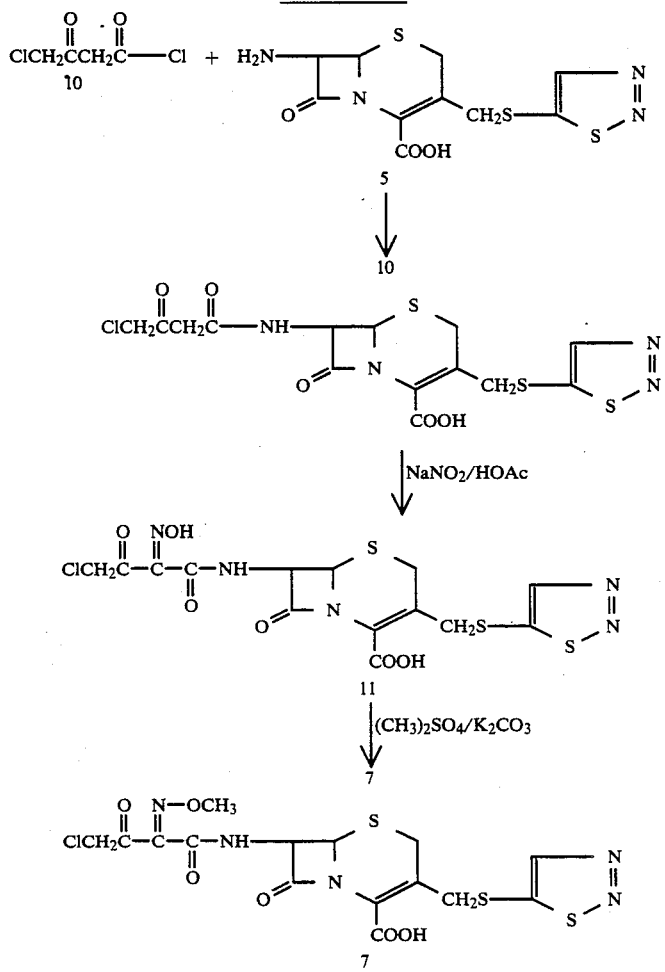

An intermediate similar to 4b has been described by Farge, et al. (U.S. Pat. No. 4,307,230) as shown on Scheme V. The disadvantages of this approach are that it is longer and also step 3 is very inefficient, i.e., 52 g of starting oximino ester gave only 8.9 g of the oximino acid.

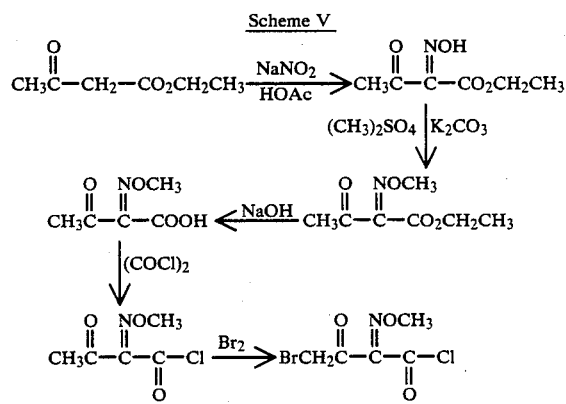

(1) A stable crystalline compound 4 was prepared in three steps from a commercially available starting material 1 (Scheme I).

(2) This compound can be used to prepare intermediates useful for the preparation of important cephalosporin antibiotics (compound 7 (Scheme II).

EXAMPLE 1 t-Butyl 4-chloro-2-(Z)-hydroxyimino-3-oxobutanoate

A solution of 35.6 g of sodium nitrite in 100 ml of water was added to a cold solution of t-butyl 4-chloro-3-oxobutanoate (100.9 g, 0.439 moles of 84% material*) in 400 ml of acetic acid containing 50 ml of water over a 0.5 hour period with stirring. The mixture was stirred in the cold for an additional hour, then stored in the cold overnight. The mixture was diluted with 500 ml portions of water, 500 ml of saturated sodium bicarbonate, 500 ml of water and 500 ml of brine, then dried over magnesium sulfate and evaporated to give an amber oil; yield 88.6 g (91% yield). This material was used in the next step without further purification. ,6 *This compound was obtained from Lonza Chemical Co., Fair Lawn, N.J.

EXAMPLE 2 t-butyl 4-chloro-2-(Z)-methoximino-3-oxobutanoate

Dimethyl sulfate (35.0 ml, 0.370 mol.) was added dropwise over a one hour period to a cold, stirred mixture of t-butyl 4-chloro-2-(Z)-hydroxyimino-3-oxobutanoate (85.7 g, 0.386 mol.) and potassium carbonate (71.5 g, 0.518 mol.) in 500 ml of dry acetone. The mixture was stirred for an additional 3.0 hours in the cold, poured into 500 ml of water and extracted with two 500 ml aliquots of ethyl acetate. The combined ethyl acetate extracts were washed with water and brine then dried over magnesium sulfate. Evaporation of the ethyl acetate at reduced pressure afforded an oil which was purified by flash chromatography on silica gel 60 using ethyl acetate:hexane (1:4) as the eluent to give 44.4 g (51%) of an oil which crystallized after standing at room temperature for several days: IR (neat, cm$^{-1}$) 1720 and 1740 (C=0): NMR (CDCL$_3$) 1.54 [S, 9H, —C(CH$_3$)$_3$], 4.11 (S, 3H, —OCH$_3$), 4.58 (S, 2H, —CH$_2$—). Anal: Calcd. for C$_9$H$_{14}$No$_4$Cl: C, 45.87; H, 5.99; N, 5.94; Cl, 15.04. Found: C. 45.25; H, 5.95; N, 5.98; Cl, 15.26.

EXAMPLE 3

4-Chloro-2-(Z)-methoxyimino-3-oxobutanoic acid

A solution of t-butyl 4-chloro-2-(Z)-methoxyimino-3-oxobutanoate (8.65 g, 0.0367 mol.) in 50 ml of methylene chloride and 50 ml of trifluoroacetic acid was stirred at room temperature for 4 hours. Added 15 ml more of trifluoroacetic acid and stirred for an additional 1.25 hours, then evaporated to dryness at reduced pressure (30° C.) The residue was dissolved in 50 ml of methylene chloride, evaporated (30° C.) and the residue was crystallized using methylene chloride:hexane to give 4.40 g (67%) of a crystalline solid, mp 91°-93° C. IR (KBr, cm$^{-1}$) 1705 and 1725 (C=0): NMR (CDCl$_3$) δ 4.20.(S, 3H, —OCH$_3$), 4.63 (S, 2H, —CH$_2$—), 11.11 (S, 1H, —OH). Anal: Calcd. for C$_5$H$_6$NO$_4$Cl: C, 33.51; H, 3.38; N, 7.81; Cl, 19.81. Found: C, 33.21; H, 3.16; N, 7.90; Cl, 19.63.

EXAMPLE 4

7β-[4-Chloro-2-(Z)-methoxyimino-3-oxobutyramido]-3-[(1,2,3-thiadiazol-5-yl)thiomethyl]ceph-3-em-4-carboxylic acid

Method A

Oxalyl chloride (0.87 ml, 10 mmol.) was added dropwise to an ice cold solution of 4-chloro-2-(Z)-methoxyimino-3-oxobutanoic acid (1.79 g, 10 mmol.) and pyridine (0.81 ml, 10 mmol.) in 50 ml of methylene chloride. The mixture was stirred in the cold for 15 minutes, at room temperature for 15 minutes, then evaporated to dryness at reduced pressure (30° C.). The residue was dissolved in 50 ml of methylene chloride and added, over 30 minutes, to an ice cold (ice/methanol bath) solution of 7-amino-3-[(1,2,3-thiadiazol-5-yl)thiomethyl]-ceph-3-em-4-carboxylic acid (3.30 g, 10 mmol.) and bis trimethylsilylacetamide (10 ml, 40.5 mmol.) in 100 ml of ethyl acetate (which had previously been stirred at room temperature for 6 hours). The mixture was stirred in the cold for an additional 15 minutes, then at room temperature for 30 minutes, and poured into a mixture of 100 ml of ethyl acetate and 50 ml of water. The resulting mixture was filtered to remove some insoluble material, the filtrate was separated and the ethyl acetate layer was extracted with four 100 ml aliquots of water then dried over magnesium sulfate. The ethyl acetate was filtered through hydrous magnesium silicate and then stirred with 150 ml of 0.2N sodium bicarbonate solution. The layers were separated and the organic phase was re-extracted with 50 ml of 0.2N sodium bicarbonate solution. The combined aqueous layers were acidified to pH 2.2 with 4N hydrochloric acid and extracted with two 100 ml portions of ethyl acetate. The ethyl acetate solution was washed with water and brine then dried over magnesium sulfate. Evaporation of ethyl acetate afforded the desired product (1.64 g) as a light yellow glass. IR (KBr, cm$^{-1}$) 1780, 1755, and 1675; NMR (DMSO-d$_6$) δ 3.70 (pair of doublets, 2H, J=17.9 Hz, endocyclic —CH$_2$S—), 4.05 (S, 3H, —OCH$_3$), 4.25 (pair of doublets, 2H, J=15 Hz, exocyclic —CH$_2$—S—), 4.85 (S, 2H, ClCH$_2$—), 5.20 (d, 1H, J=3.7 Hz, 6H of 7ACA), 5.80 (double doublet, 1H, J=3.7 and 8.4 Hz, 7H of 7ACA), 8.89 (S, 1H, thiadiazole H), 9.48 (d, 1H, J=8.4 Hz, —NH).

Method B 2-(Trimethylsilyl)ethoxymethyl 7β-[4-chloro-2-(Z)-methoxyimino-3-oxobutyramido-3-[(1,2,3-thiadiazol-5-yl)thiomethyl]ceph-3 -em-carboxylate (1.5 g, 2.41 mmol.) was stirred in 25 ml of trifluoroacetic acid for 1.0 hour at room temperature. The solution was evaporated to dryness at 40° C. and the residue dissolved in methylene chloride and again evaporated at reduced pressure. The residue was partitoned in 75 ml of ethyl acetate and 150 ml of 0.2N sodium bicarbonate solution. The layers were separated and the ethyl acetate was extracted with 25 ml more of 0.2N sodium bicarbonate solution. The combined aqueous portions were acidified to pH 2.5 and extracted with 75 ml aliquots of ethyl acetate. The combined ethyl acetate extracts were washed with brine, dried over magnesium sulfate and evaporated to give 0.83 g (75%) of a yellow glass.

Method C

Diphenylmethyl 7 -[4-chloro-2-(Z)-methoxyimino-3-oxobutyramido]-3-[(1,2,3-thiadiazol-5-yl)thiomethyl]-ceph-3-em-4-carboxylate (3.25 g, 4.94 mmol.) was treated in the same manner as described in Method B to afford 2.11 g (87%) of the desire product.

EXAMPLE 5

2-(Trimethylsilyl)ethoxymethyl 7-amino-3-[(1,2,3-thiadiazol-5-yl)thiomethyl]ceph-3-em-4-carboxylate A mixture of 7-amino-3-[(1,2,3-thiadiazol-5-yl)thiomethyl]ceph-3-em-4-carboxylic acid (3.30 g, 10 mmol.) and triethylamine (1.40 ml, 10 mmol.) in 50 ml of dimethylformamide was stirred at room temperature for 1 0 hour. Trimethylsilylethoxymethyl chloride (1.80 ml, 10 mmol.) was added dropwise, the reaction mixture was stirred for 15 minutes at room temperature then poured into 100 ml of water and extracted with 80 ml of ethyl acetate. The ethyl acetate extract was washed with 75 ml aliquots of saturated sodium bicarbonate, water and brine then dried over magnesium sulfate. Evaporation of the solvent afforded 3.05 g of product as an amber oil: NMR (CDCl$_3$) δ 0.03 [S, 9H, Si(CH$_3$)$_3$], 0.95 (t, 2H, J=7.5 Hz, —CH$_2$Si), 2.00 (S, 2H, NH$_2$), 3.50 (m, 4H, —OCH$_2$Si and indocyclic —CH$_2$—S—), 4.00 (S, 2H, oxocyclic —CH$_2$S—), 4.60 (d, 1H, J=5.0 Hz, 6H of 7ACA), 4.80 (d, 1H, J=5.0 Hz, 7H of 7ACA), 5.30 (S, 2H, —OCH$_2$O—), 8.40 (S, 1H, thiadiazole H).

EXAMPLE 6

Diphenylmethyl 7β-[4-chloro-2-(Z)-methoxyimino-3-oxobutyramido]-3-[(1,2,3-thiadiazol-5-yl)thiomethyl]ceph-3-em-4-carboxylate A solution of 4-chloro-2-(Z)-methoxyimino-3-oxobutanoic acid (4.05 g, 22.6 mmol.), diphenylmethyl 7-amino-3-[(1,2,3-thiadiazol-5-yl)thiomethyl]ceph-3-em-4-carboxylate (11.2 g, 22.6 mmol.) and 1-ethoxycarbonyl-2-ethoxy-1,2-dihydroquinoline (5.58 g, 22.6 mmol.) in 200 ml of methylene chloride was stirred at room temperature for 3 hours. The solution was evaporated to dryness at reduced pressure and the residue was taken up in 150 ml of ethyl acetate which was extracted with 50 ml aliquots of 1N hydrochloric acid, water, saturated sodium bicarbonate, water and brine. The ethyl acetate was dried over magnesium sulfate, evaporated to dryness and the resulting product was purified by flash chromatography on silica gel 60 using ethyl acetate: hexane (1:2) as the eluent to afford 3.34 g of the desired compound:NMR (CDCl$_3$) δ 3.52 (pair of d, 2H, J=18 Hz, endocyclic —CH$_2$S—), 4.05 (pair of d, 2H, J=13 Hz, exocyclic —CH$_2$S—), 4.15 (S, 3H, —OCH$_3$)j, 4.59 (S, 2H, ClCH$_2$—), 5.04 (d, 1H, J=4.7 Hz, 6H of 7ACA), 5.88 (dd, 1H, J=4.7 and 8.6 Hz, 7H of 7ACA), 6.89 (S, 1H, —CH—), 7.33 (m, 10H, aromatic H), 8.37 (S, 1H, thiadiazole H).

EXAMPLE 7

2-(Trimethylsilyl)ethoxymethyl 7β-[4-chloro-2-(Z)-methoxyimino-3-oxobutyramido]-3-[(1,2,3-thiadiazol-5-yl)thiomethyl]ceph-3-em-4-carboxylate A solution of 4-chloro-2-(Z)-methoxyimino-3-oxobutanoic acid (2.17 g, 4.77 mmol.), 2-(trimethylsilyl)ethoxymethyl 7-amino-3-[(1,2,3-thiadiazol-5-yl)thiomethyl]ceph-3-em-4-carboxylate (0.85 g, 4.77 mmol.), and 1-ethoxycarbonyl-2-ethoxy-1,2-dihydroquinoline (1.18 g, 4.77 mmol.) in 40 ml of methylene chloride was stirred at room temperature for 3 hours then worked up as described in Example 6 to afford 0.615 g of the ester. NMR (CDCl$_3$) δ 0.03 [S, 9H, —Si(CH$_3$)$_3$], 0.97 (t, 2H, J=7.5 Hz, —CH$_2$Si—), 3.62 (pair of d, 2H, J=18 Hz, endocyclic —CH$_2$S—), 3.75 (m, 2H, —OCH$_2$—), 4.17 (pair of d, 2H, J=13.3 Hz, exocyclic —CH$_2$S), 4.18 (S, 3H, —OCH$_3$), 4.63 (S, 2H, —ClCH$_2$—), 5.07 (d, 1H, J=4.9, 6H of 7ACA), 5.38 (pair of d, 2H, J=6.0 Hz, —OCH$_2$O), 5.87 (dd, 1H, J=4.9 and 8.5 Hz, 7H of 7ACA), 7.22 (d, 1H, J=8.5 Hz, —NH—), 8.52 (S, 1H, thiadiazole H).

EXAMPLE 8

2-(Trimethylsilyl)ethoxymethyl 7β-[2-(2-aminothiazol-4-yl)-(Z)-2-methoxyiminoacetamido]-3-[(1,2,3-thiadiazol-5-yl)thiomethyl]-ceph-3-em-4-carboxylate

Method A

A solution of 2-(trimethylsilyl)ethoxymethyl 7β-[4-chloro-2-(Z)-methoxyimino-3-oxobutyramido]-3-[(1,2,3-thiadiazol-5-yl)thiomethyl]ceph-3-em-4-carboxylate (622 mg, 1 mmol.) and thiourea (76 mg, 1 mmol.) in 8 ml of dimethylacetamide was stirred at room temperature overnight. The reaction mixture was diluted with 50 ml of ethyl acetate and extracted with dilute sodium bicarbonate, water and brine. The ethyl acetate solution was dried over magnesium sulfate, evaporated at reduced pressure, and the resulting product was purified by preparative thick layer chromatography on silica gel using ethyl acetate:hexane (2:1) as the eluent to afford 124 mg of the desired product: NMR (DMSO-d$_6$+CDCl$_3$) δ 0.03 [S, 9H, —Si(CH$_3$)$_3$], 0.96 (t, 2H, J=7.5 Hz, —CH$_2$Si—), 3.62 (S, 2H, endocyclic —CH$_2$S—), 3.74 (t, 2H, J=7.5 Hz, —OCH$_2$Si—), 4.02 (S, 3H, —OCH$_3$), 4.15 (pair of doublets, 2H, J=13.4 Hz, exocyclic —CH$_2$—S), 5.12 (d, 1H, J=4.7 Hz, 6H of 7ACA), 5.37 (m, 2H, —OCH$_2$O), 5.90 (double doublet, 1H, J=8.4 and 4.7 Hz, 7H of 7ACA), 6:15 (S, 2H, —NH$_2$), 6.80 (S, 1H, thiadiazole H), 8 55 (S, 1H, thiadiazole H), 9.15 (d, 1H, J=8.4 Hz, —NH—).

Method B

A solution of sodium 7β-[2-(2-aminothiazol-4-yl)-(Z)-2-methoxyiminoacetamido]-3-[(1,2,3-thiadiazol-5-yl)thiomethyl]ceph -3-em-4-carboxylate (535 mg, 1 mmol.) and 2-(trimethylsilyl)ethoxymethyl chloride (0.18 ml, 1 mmol.) in 5 ml of dimethylformamide was stirred at room temperature for 5 minutes. The mixture was diluted with 50 ml of ethyl acetate and extracted with dilute sodium bicarbonate, water and brine, then dried over magnesium sulfate. Evaporation of the solvent afforded 535 mg of product. The infrared and nuclear magnetic resonance spectra were the same as the material described in Method A.

EXAMPLE 9

7β-[2-(2-Aminothiazol-4-yl)-(Z)-2-methoxyiminoacetamido]-3-[(1,2,3-thiadiazol-5-yl)thiomethyl]-ceph-3-em-4-carboxylic acid A solution of 7β-[4-chloro-2-(Z)-methoxyimino-3-oxobutyramido]-3-[(1,2,3-thiadiazol-5-yl)thiomethyl]-ceph-3-em-4-carboxylic acid (254 mg, 0.52 mmol.) and thiourea (80 mg, 1.05 mmol.) in 8 ml of dimethylacetamide was stirred at room temperature overnight then poured into 20 ml of ice water. The pH was adjusted to 3.5 with dilute sodium bicarbonate and the product was collected by filtration, yield 125 mg.

What is claimed is:

1. A process for producing 4-chloro-2-(Z)-methoxyimino-3-oxobutanoic acid which comprises the steps of:
    (a) treating t-butyl 4-chloro-3-oxobutanoate with sodium nitrite or nitrous acid to produce t-butyl 4-chloro-2-(Z)-hydroximino-3-oxobutanoate;
    (b) treating t-butyl 4-chloro-2-hydroxyinino-3oxobutanoate with dimethyl sulfate and potassium carbonate to produce t-butyl 4-chloro-2-(Z)-methoxyimino-3-oxobutanoate; and
    (c) treating t-butyl 4-chloro-2-(Z)-methoxyimino-3-oxobutanoate with trifluoroacetic acid to give the desired product 4-chloro-2-(Z)-methoxyimino-3-oxobutanoic acid.

* * * * *